US012496417B2

(12) United States Patent
Russo et al.

(10) Patent No.: US 12,496,417 B2
(45) Date of Patent: Dec. 16, 2025

(54) ENDOTRACHEAL TUBE POSITIONING MECHANISM

(71) Applicant: DALE MEDICAL PRODUCTS, INC., Franklin, MA (US)

(72) Inventors: Ronald D. Russo, Naples, FL (US); João Casimiro de Pina Lima, Central Falls, RI (US)

(73) Assignee: DALE MEDICAL PRODUCTS, INC., Franklin, MA (US)

( * ) Notice: Subject to any disclaimer, the term of this patent is extended or adjusted under 35 U.S.C. 154(b) by 780 days.

(21) Appl. No.: 17/725,186

(22) Filed: Apr. 20, 2022

(65) Prior Publication Data

US 2022/0331536 A1 Oct. 20, 2022

Related U.S. Application Data

(60) Provisional application No. 63/177,004, filed on Apr. 20, 2021.

(51) Int. Cl.
*A61M 16/04* (2006.01)
*A61M 25/02* (2006.01)

(52) U.S. Cl.
CPC .... *A61M 16/0497* (2013.01); *A61M 16/0493* (2014.02); *A61M 25/02* (2013.01)

(58) Field of Classification Search
CPC .......... A61M 16/0497; A61M 16/0488; A61M 16/0493; A61M 25/02; A61M 2205/02; A61M 2209/088; A61M 2210/0625
See application file for complete search history.

(56) References Cited

U.S. PATENT DOCUMENTS 6,578,576 B1 * 6/2003 Taormina .............. A61M 25/02 128/207.14
8,591,445 B2 * 11/2013 Serola ..................... A61F 5/028 602/5
2006/0118120 A1 * 6/2006 Russo ............... A61M 16/0497 128/207.14
2016/0121067 A1 * 5/2016 VanMiddendorp .......................... A61M 16/0875 128/207.17
2017/0197049 A1 * 7/2017 Doll .................. A61M 16/0497
2017/0275150 A1 * 9/2017 Taylor ........................ B68B 5/00
2020/0222651 A1 * 7/2020 Jockel ............... A61M 16/0497
2022/0288340 A1 * 9/2022 VanMiddendorp .......................... A61M 16/0497

* cited by examiner

*Primary Examiner* — Justine R Yu
*Assistant Examiner* — Matthew R Moon
(74) *Attorney, Agent, or Firm* — ARENTFOX SCHIFF LLP

(57) ABSTRACT

In endotracheal tube positioning device for providing fixed positioning and slidable repositioning of a patient's endotracheal tube within a patient's oral cavity includes a neckband, slide track member, a bracket for securement of the tube, and a flexible overlay strip. The slide track member, bracket, and overlay strip are affixed to the neckband. The device permits slidable side-to-side adjustment of the secured endotracheal tube within the patient's oral cavity without having to remove or detach the neckband from around the patient's neck. The bracket can be secured to the endotracheal tube by with an adhesive backed tape or a tube securement strap having engagement elements mating with an adhesive backed patch adhered to the endotracheal tube.

20 Claims, 9 Drawing Sheets

ENDOTRACHEAL TUBE POSITIONING MECHANISM

RELATED APPLICATIONS

This application, claims priority to, and the benefit of, U.S. Provisional Patent Application No. 63/177,004, which was filed Apr. 20, 2021, and which is titled “ENDOTRACHEAL TUBE POSITIONING MECHANISM”, the contents of which are incorporated herein by this reference for all purposes.

FIELD OF THE INVENTION

The subject application relates to medical devices and, more particularly to endotracheal tubes, and a device for positioning and repositioning endotracheal tubes when used with a patient.

BACKGROUND OF THE INVENTION

Medical endotracheal tubes and holders have been successfully utilized on intubated patients since their commercial introduction. Once such product is the Model No. 270 Endotracheal Tube Holder, commercially available from Dale Medical Products, Inc. of Franklin, MA 02038. U.S. Pat. No. 8,096,300 titled “Endotracheal Tube Holder” issued Jan. 17, 2012, hereinafter referred to as the ’300 patent or ’300 holder, further describes such an endotracheal tube holder.

The ’300 holder is intended to maintain the endotracheal tube securely within a patient’s oral cavity and to prevent inward or outward movement of the endotracheal tube relative to patient’s oral cavity. However, newer medical protocol requires positioning and repositioning of the endotracheal tube, typically left, center, or right, within a patient’s oral cavity to prevent mouth, lip, and/or tongue pressure sores caused by leaving the endotracheal tube in one position longer than 8 hours. As such, side to side repositioning of the endotracheal tube within the patient’s oral cavity is routinely and repeatedly required. Ideally, the endotracheal tube side to side repositioning procedure should be performed at least three times per day while still trying to maintain tube security and fixation. However, the ’300 holder requires removal of the neckband from around the patient’s neck and separation of the neckband from the facial anchoring device to accomplish side to side movement of the tube within the patient’s oral cavity or to perform oral hygiene.

Accordingly, a need exists for a mechanism that permits easy side to side repositioning of the endotracheal tube within the patient’s oral cavity.

In an additional need exists for a mechanism that permits rapid side to side repositioning of the endotracheal tube within the patient’s oral cavity.

A further need exists for a mechanism that permits side to side movement of the endotracheal tube within the patient’s oral cavity, without having to disengage the neckband.

SUMMARY OF THE INVENTION

An endotracheal tube positioning device for providing fixed positioning and slidable repositioning of a patient’s endotracheal tube within a patient’s oral cavity comprises a neckband, slide track member, a bracket for securement of the tube, and a flexible overlay strip. The slide track member, bracket, and overlay strip are affixed to the neckband.

The device permits slidable side-to-side adjustment of the secured endotracheal tube within the patient’s oral cavity without having to remove or detach the neckband from around the patient’s neck. The bracket can be secured to the endotracheal tube by with an adhesive backed tape or a tube securement strap having engagement elements mating with an adhesive backed patch adhered to the endotracheal tube.

According to one aspect of the disclosure, an endotracheal tube securement apparatus comprises: a platform securable proximate a patient’s oral cavity and having a forward facing surface, a slide track member having a rearward facing surface securable to the platform forward facing surface, and a bracket retained between the platform forward facing surface and the slide track member rearward facing surface, the bracket being movable over the slide track member. In embodiments, the bracket defines a loop into which the slide track member is insertable. In embodiments, the apparatus of further comprises a retention strip having at least one end removably securable to one of the platform forward facing surface or a forward facing surface of the slide track member. In embodiments, the apparatus of further comprises an anchor member having a rearward facing surface configured for securing the platform above the patient’s lips.

According to another aspect of the disclosure, an endotracheal tube securement apparatus comprises: a platform securable proximate a patient’s oral cavity and having a forward facing surface, a bracket having a generally L-shaped profile with a first leg extending along an axis and securable to the endotracheal tube, the bracket further having a second leg retained relative to the platform forward facing surface but slidably movable in directions normal to the axis. In embodiments, the apparatus of further comprises a slide track member having a rearward facing surface securable to the platform forward facing surface wherein the second leg of the bracket defines a loop into which the slide track member is inserted.

According to yet another aspect of the disclosure, a kit for use in securing an endotracheal tube to a patient comprises: an anchor having a rearward facing surface securable to a patient’s skin; a neck band having a rearward facing surface removably securable to the anchor and a forward facing surface to which a bracket is movably attached over a slide track member, the slide track having first and second ends secured to the neck band forward facing surface, and a retention strip having at least one end removably securable to one of the neckband forward facing surface or a forward facing surface of the slide track member.

BRIEF DESCRIPTION OF THE DRAWINGS

The various features and advantages of the present invention may be more readily understood with reference to the following detailed description taken in conjunction with the accompanying drawings, wherein like reference numerals designate like structural elements.

DETAILED DESCRIPTION OF THE INVENTION

Figure 1:
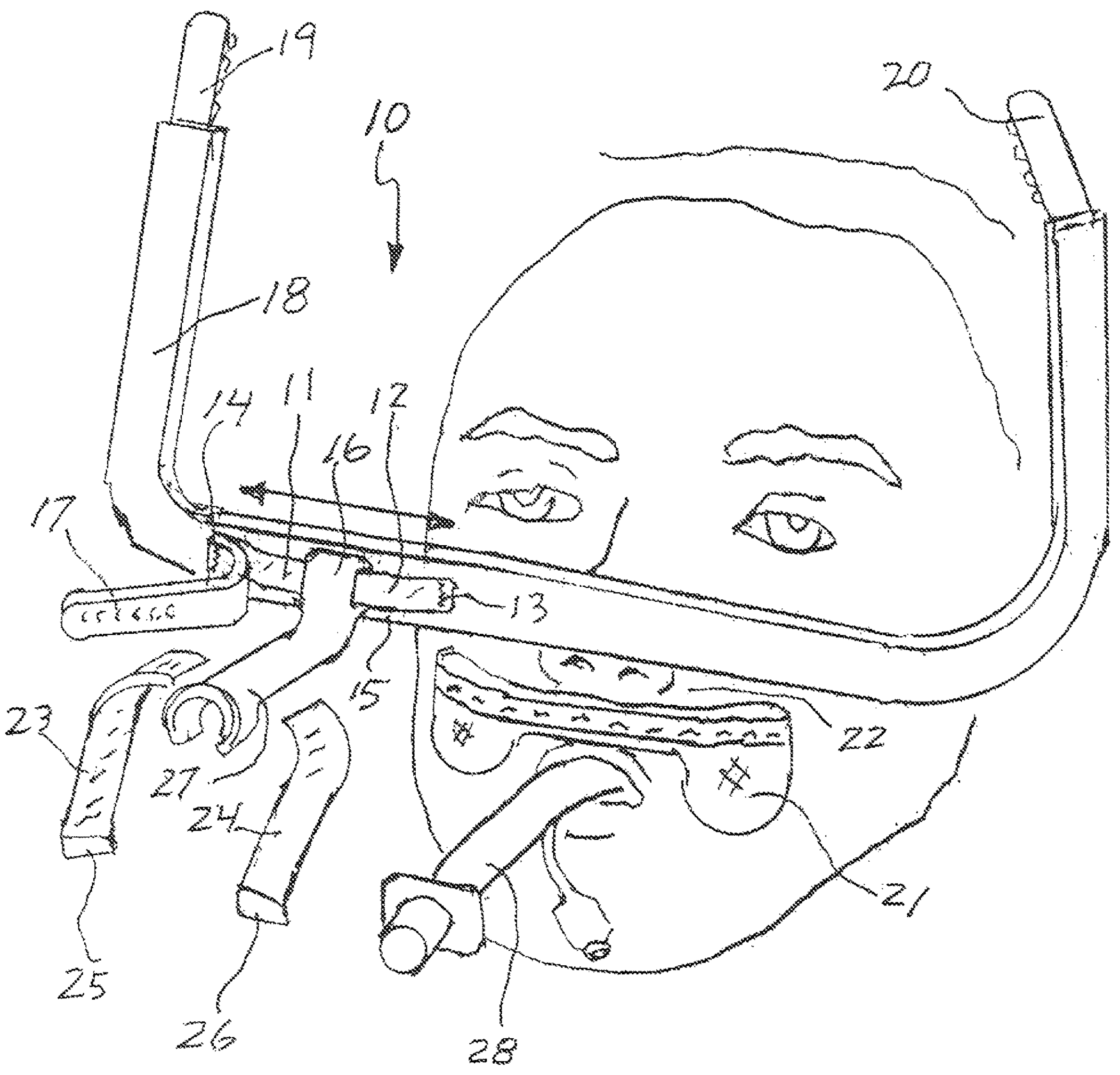
FIG. 1 is a perspective view of the an endotracheal tube holder system in accordance with one aspect of the disclosure.

Embodiments of the systems and methods are described in detail with reference to the drawings in which like reference numerals designate identical or corresponding elements in each of the several views. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so. Further, words denoting orientation such as "top", "bottom", "side", "lower", "upper", "front" and "back" and the like, as well as references on a specific axis in three-dimensional space are merely used to help describe the location of components with respect to one another. No words denoting orientation are used to describe an absolute orientation, i.e., where an "upper" part must always be on top.

FIG. 1 illustrates conceptually an endotracheal tube assembly 10 according to embodiments fore use with an endotracheal tube holder system 11. Assembly 10 comprises a neckband 18, which can be extended over the patient's cheeks and secured behind a patient's head or neck region using hook securement tabs 19 and 20. A face anchoring device 21 anchors neckband 18 in place on the patient's upper lip 22. Neckband 18 extends about the patient's head and neck. A portion of neckband 18, neckband platform 15, defines a surface to which system 11 is attachable. System 11 comprises a slide track member 12, bracket 16 and retention strip 17, as illustrated. Slide track member 12, bracket 16, and overlay strip 17 form the basic components of system 11 and are discussed in greater detail in further drawings.

Slide track member 12 may be implemented with a substantially flat rectangular or ribbon-shaped piece of material having ends 13 and 14 thereof secured to neckband platform 15. Ends 13 and 14 may be secured to neckband platform 15 by sew, adhesive, or other process, such as sonic welding, depending on the nature and composition of the materials comprising member 12. Slideably mounted onto slide track member 12 is bracket 16. Overlaying both slide track member 12 and bracket 16 is flexible overlay retention strip 17.

Figure 2:
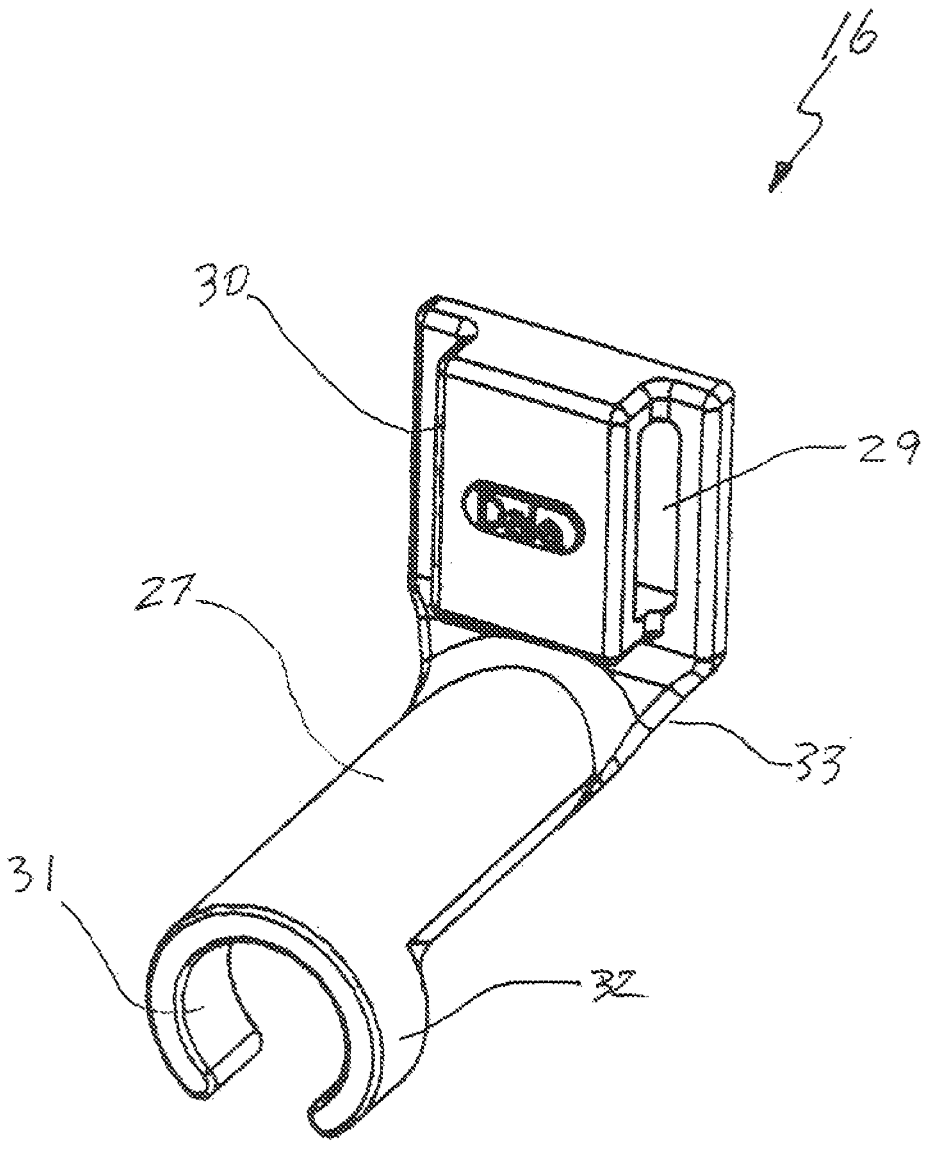
FIG. 2 is a perspective view of the bracket portion of the system in accordance with one aspect of the disclosure.

FIG. 2 illustrates conceptually bracket 16 in greater detail. In embodiments, bracket 16 may have a generally L-shaped profile with a first leg extending along an axis 90 and securable to the endotracheal tube, the bracket further having a second leg retained relative to the platform 15 forward facing surface but slidably movable in directions normal to the axis. Bracket 16 has a loop defined by apertures 29 and 30 formed on the shorter leg thereof, and into which slide track member 12 can be threaded, and an arcuate bracket extension 27 formed on the longer leg thereof to accommodate the endotracheal tube. In embodiments, bracket 16 may have a molded-in rearward curve 33 which prevents any upper lip 22 contact to prevent any pressure sores from being caused by bracket 16. Bracket 16 can be injection molded from a semi flexible plastic, such as DEHP free Colorite PVC resin of about 80 Shore A durometer.

Figure 3:
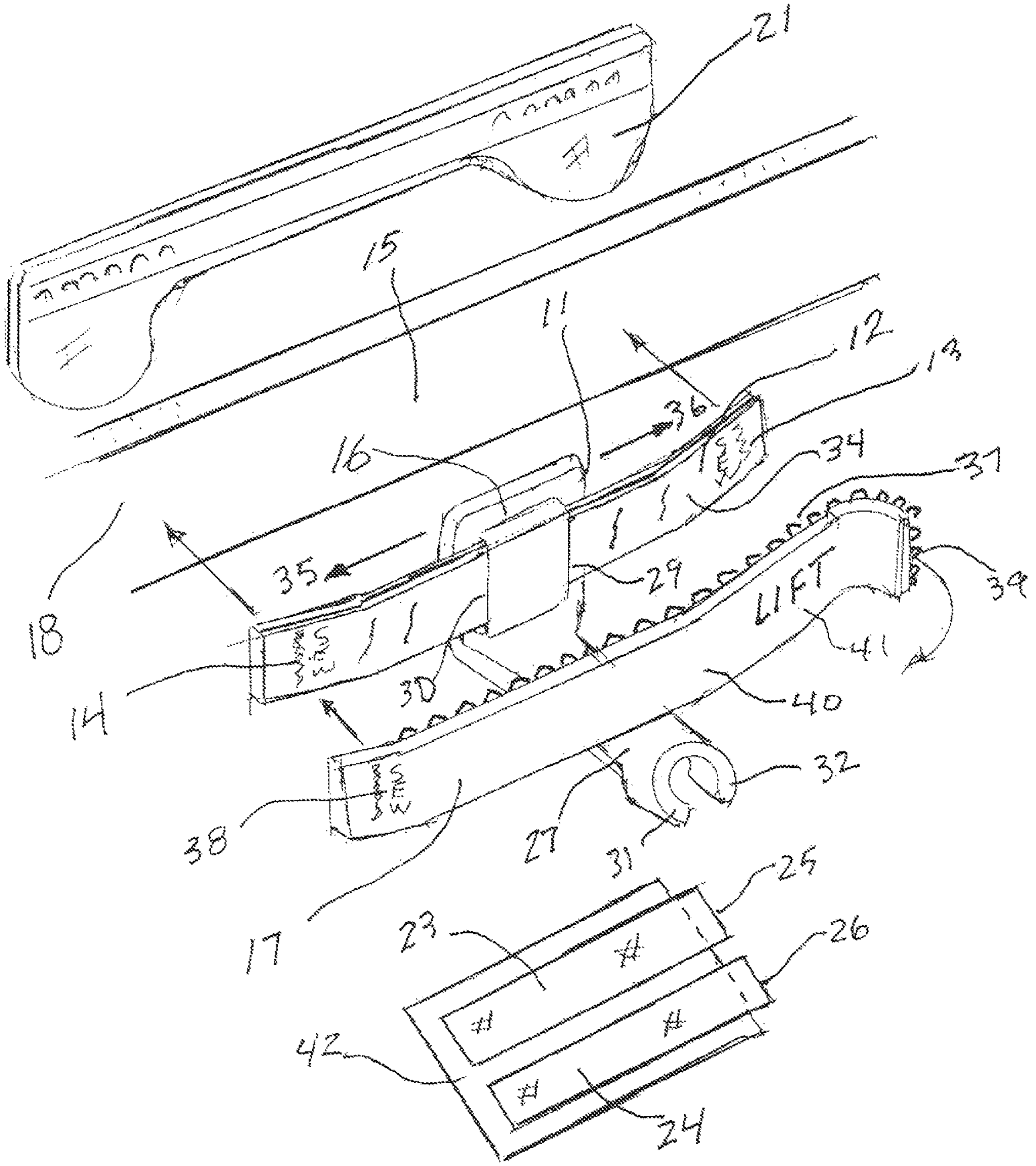
FIG. 3 is an exploded perspective view of the system prior to assembly on the neckband platform of the neckband in accordance with the disclosure.

FIG. 3 is an exploded perspective view of the system 11 relative to neckband platform 15 and face anchoring device 21 prior to assembly on the neckband platform 15. Specifically, bracket 16 is slidably engaged with slide track member 12 through apertures 29 and 30. Slide track member 12 may be fabricated from a firm loop material having a frontal loop area 34. Bracket 16 is free to slide along member 12 in either direction 35 and 36. Slide track member 12 is sewn or sonic welded onto neckband platform 15 proximate ends 13 and 14. Flexible overlay retention strip 17 made from polypropylene low profile hook has a rearward hook surface area 37 which is engageable and disengageable with frontal loop surface area 34 on slide track member 12. Retention strip 17 is stitched on only one side 38 to side 14 on slide track member 12. Opposite side 39 of retention strip 17 is not sewn in place and forms a lift edge on strip 17 permitting engagement and disengagement with slide track member 12. Strip 17 may include a front facing printable surface 40 having legend 41 containing instructions or information useful to a clinician, such as "LIFT", on strip 17. Printing may include a repeat pattern of information.

Figure 4:
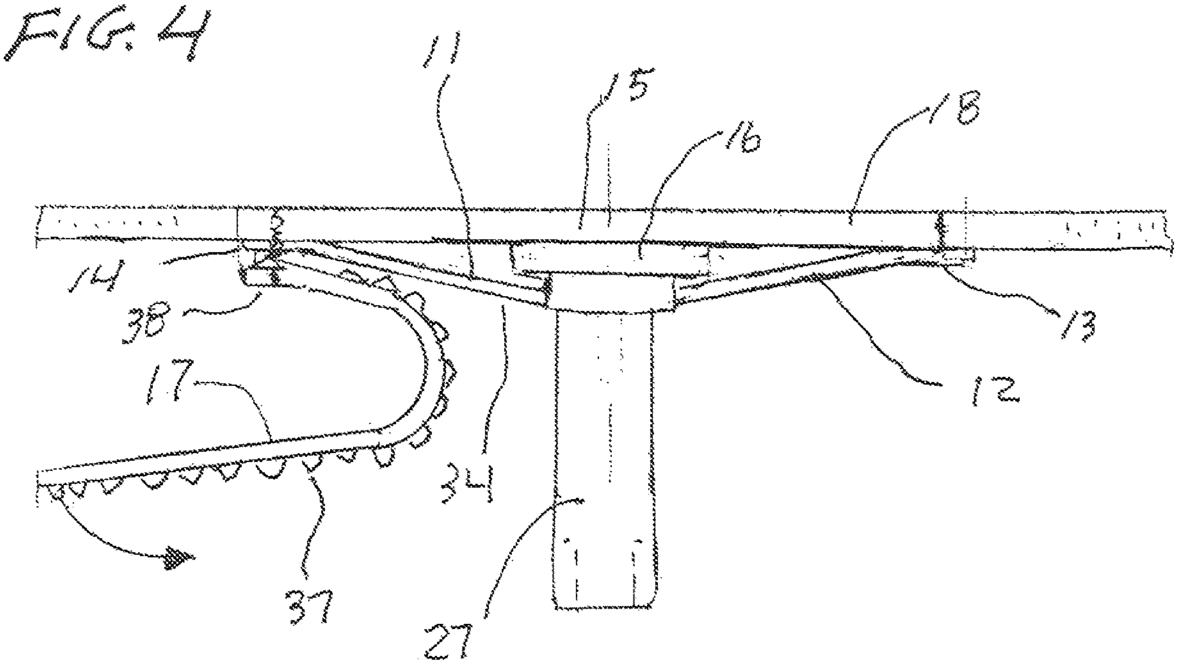
FIG. 4 is a top view of the system attached to the neckband platform in accordance with the disclosure.
Figure 5:
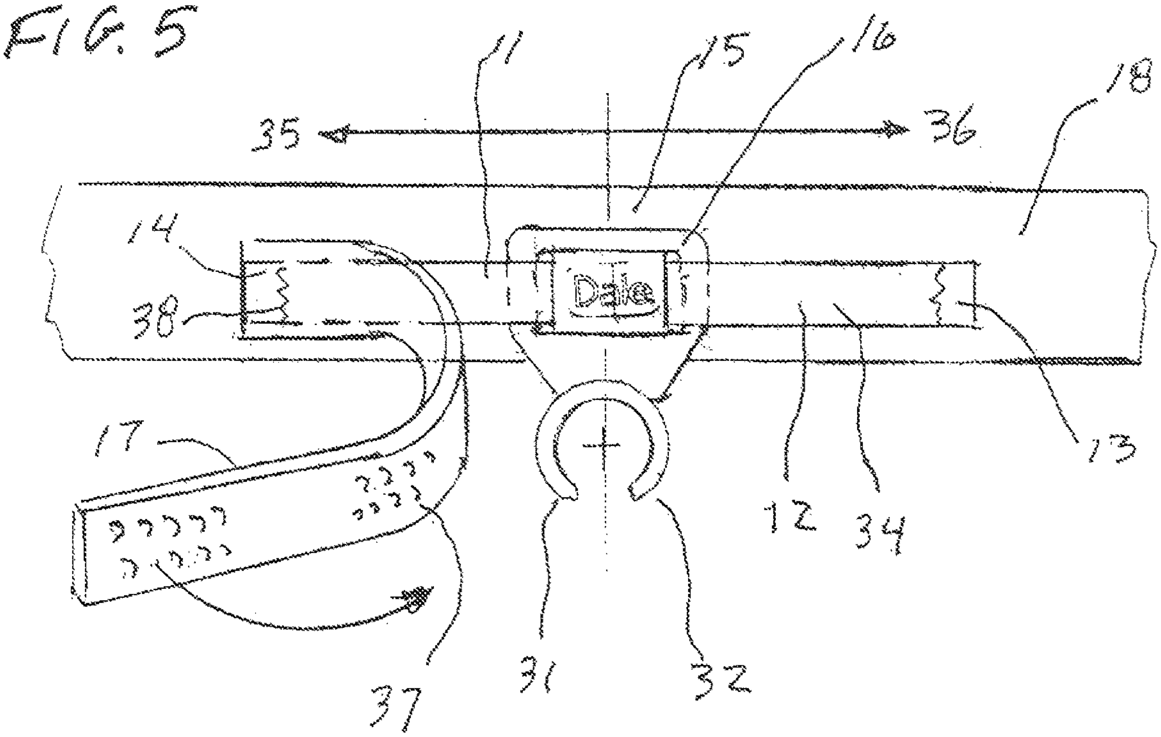
FIG. 5 is a frontal view of the system taken from a top view of the mechanism from FIG. 4.

FIGS. 4 and 5 illustrate the functional components of system 11 and how engagement and disengagement of overlay strip 17 with the slide track member 12 permits fixed positioning, slidable repositioning along the slide track member 12 to another fixed position of the bracket 16 on the slide track member 12. FIG. 4 is a top view of assembled system 11 attached to the neckband platform 15. FIG. 5 illustrates from a frontal view all the assembled elements from FIG. 3. As can be seen from both FIGS. 4 and 5, overlay strip 17 can be adhered and engaged with both slide track member 12 and neckband 18. Such adherence and engagement prevents bracket 16 from pivoting downward and the bracket 16 securely affixed to neckband 18. In use, once the rearward hook surface 37 of strip 17 is engaged with the frontal loop area 34 on slide track member 12, bracket 16 remains in a fixed retained position and cannot be easily or slidably moved. Strip 17 can be manually disengaged from slide track member 12, by lifting up and disengaging strip 17 from slide track member 12. The clinician can then permit side to side repositioning of bracket 16. Re-engagement of retention strip 17 with slide track member 12 permits the bracket 16 to be fixed in the new position.

Figure 6:
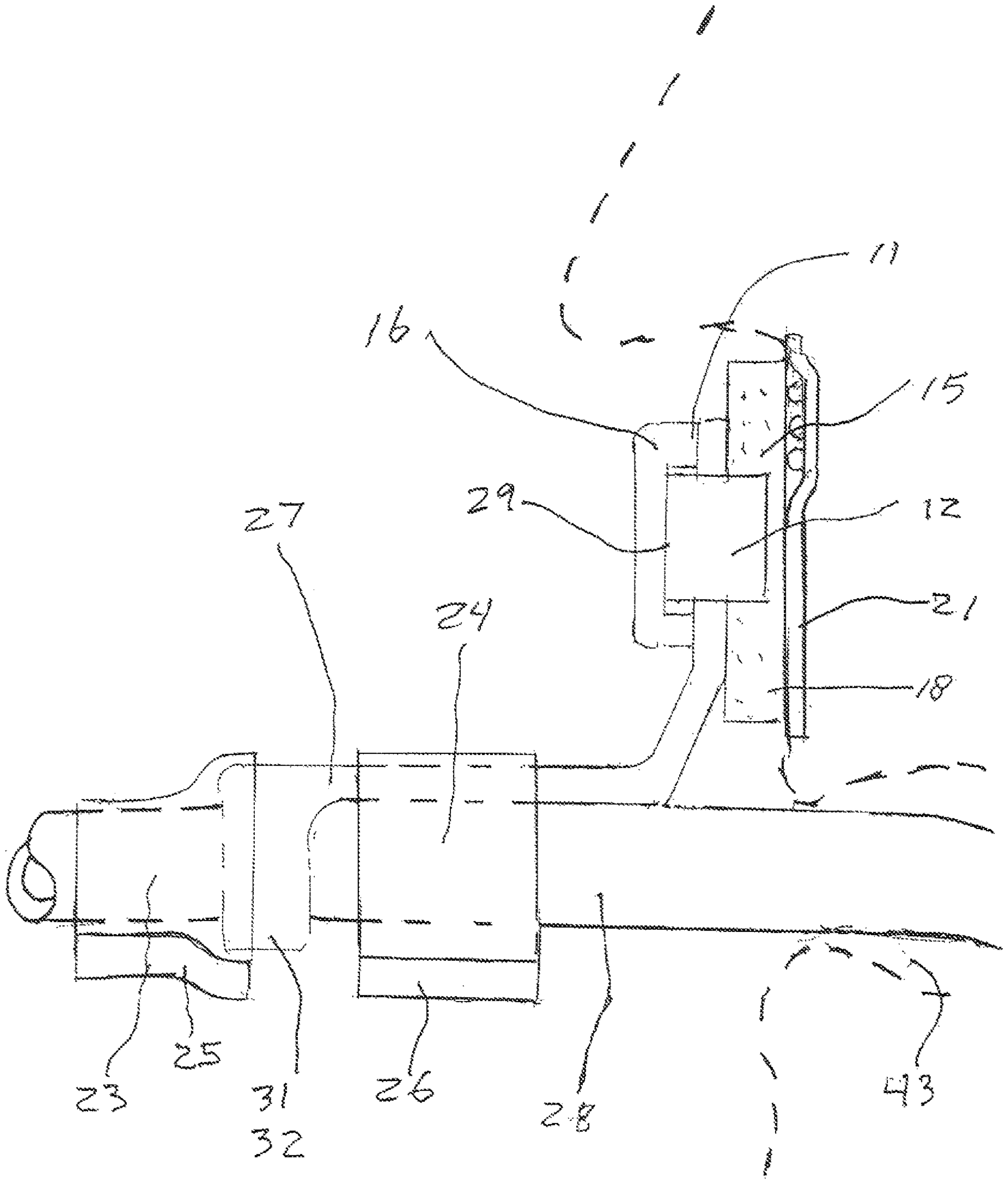
FIG. 6 is a side view of the mechanism attached to a patient's face using dual tapes to fasten the tube in place onto the bracket portion.

FIG. 6 is a side view of the system 11 attached to a patient's face using dual tapes 23 and 24 to fasten endotracheal tube 28 onto bracket extension 27. Non-adherent mylar polyester tips 25 and 26 permit a convenient graspable edge during wrapped adherence of the tapes as well as a convenient graspable edge to remove both tapes 23 and 24, if desired. Removable tapes 23 and 24 which are die cut on a back release liner 42 can be used to secure an endotracheal tube 28 in place by taping around bracket extension 27. Tape 24 can be wrapped around bracket extension 27 while the second tape 23 can be wrapped around frontal bracket tabs 31 and 32 to secure tube 28 in place and prevent inward or outward movement of the tube 28 within a patient's airway and/or oral cavity 43.

Figure 7:
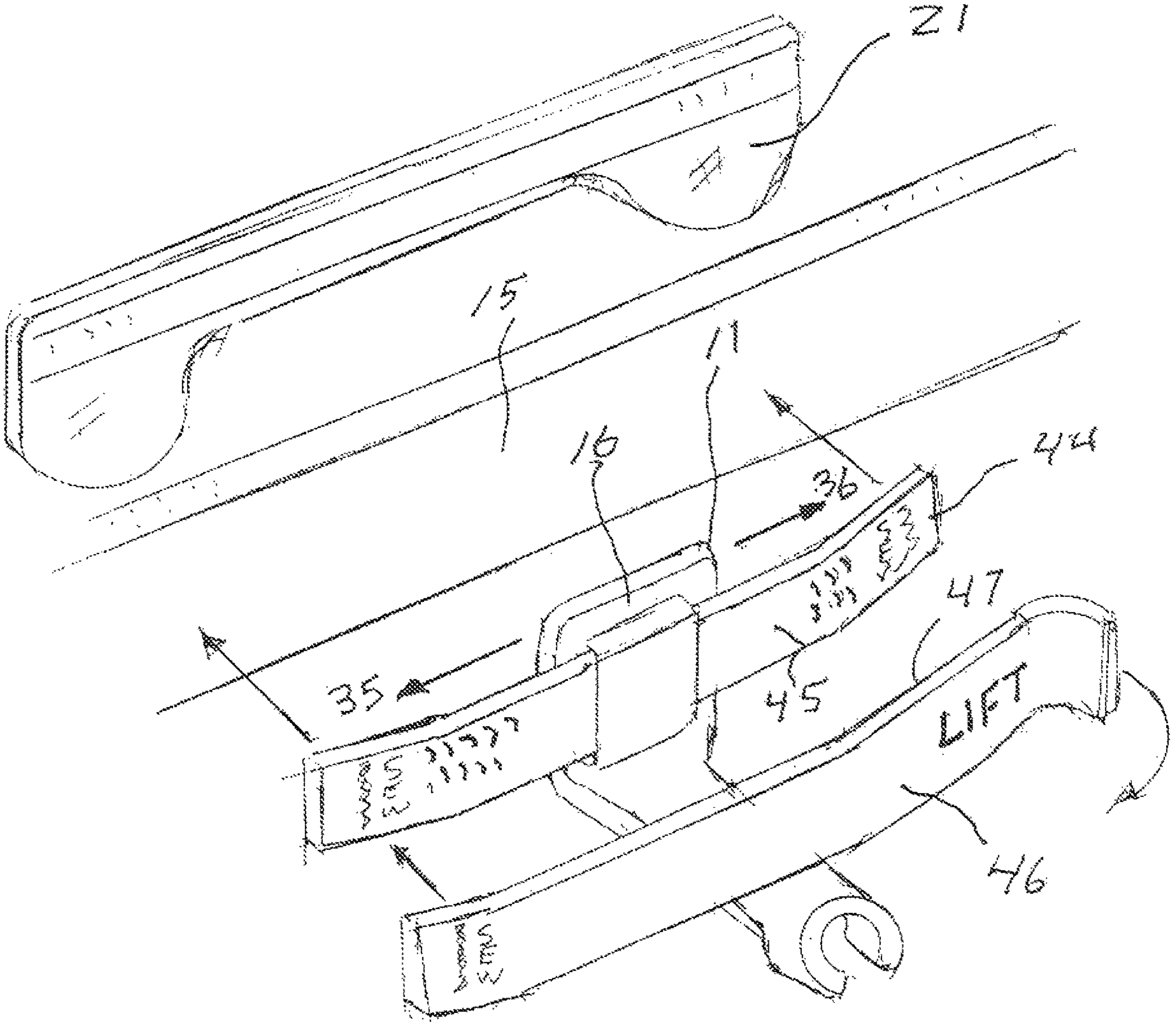
FIG. 7 is an exploded perspective view of an alternate embodiment of the mechanism.

FIG. 7 is an exploded perspective view of an embodiment of system 11 wherein slide track member 44 comprises a low profile molded hook component having a frontal hook face surface 45 and overly strip 46 comprises a loop material having a rearward engagement surface 47. This embodiment of system 11 operates in similar manner as illustrated in FIGS. 3-5 such that bracket 16 is proximate to oral cavity 43. The version illustrated in FIG. 7 may be preferred by some clinicians since the slide track member 44 utilizes a non-absorbent molded plastic hook on the bracket platform 15 which may resist oral secretions over extended use.

Figure 8:
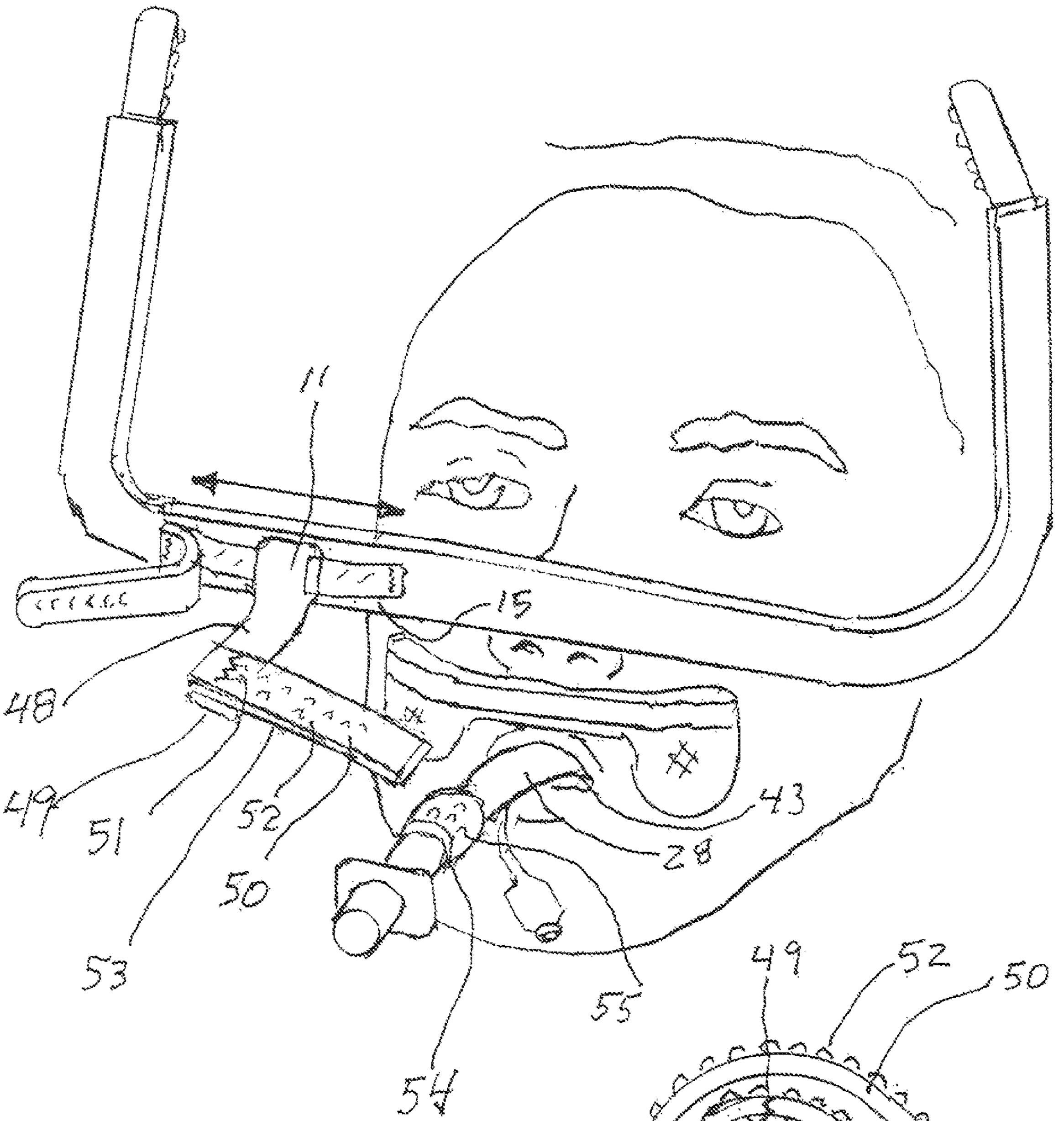
FIG. 8 is perspective view of an alternate embodiment of the mechanism with a wrap around tube securement strap as part of the bracket portion and a mating tube adhesive patch.

FIG. 8 depicts how system 11 can be modified to utilize a non-tape securement device to secure endotracheal tube 28 in place in a patient's airway oral cavity 43 as illustrated in FIG. 6. Bracket 48 may also comprise plastic molded from semi-flexible DEHP free PVC but terminates in an end portion 49 of about 0.060 inches in thickness to permit sewable or sonic weld attachment of flexible strap 50 on top 51 of strap 50. Strap 50 can be made from a variety of laminated hook and loop materials sometimes called laminated hook and loop. Strap 50 can have a top hook surface 52 engageable with underside loop material surface 53 in a wrapped manner.

Figure 9:
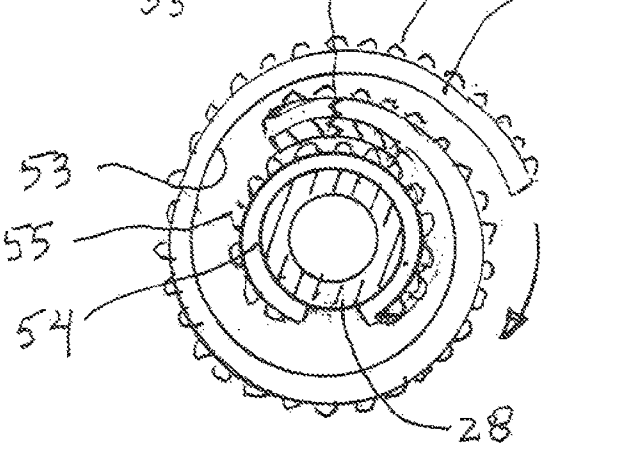
FIG. 9 is a cross section view of the tube securement strap wrapping around the mating tube adhesive patch on the endotracheal tube.

FIG. 9 illustrates in a cross sectional view how strap 50 will form an interlocking engagement with adhesive backed low profile hook patch 54 which can be adhesively applied to endotracheal tube 28. Patch 54 has a molded-in hook top surface 55 which engages with underside loop surface 53 on strap 50. This engagement to secure mechanism 11 in place on tube 28 is further illustrated in FIG. 9. Strap 50 can firmly attach mechanism 11 onto tube 28 while preserving the functional side to side adjustment of mechanism 11 within the oral cavity of a patient.

Figure 10:
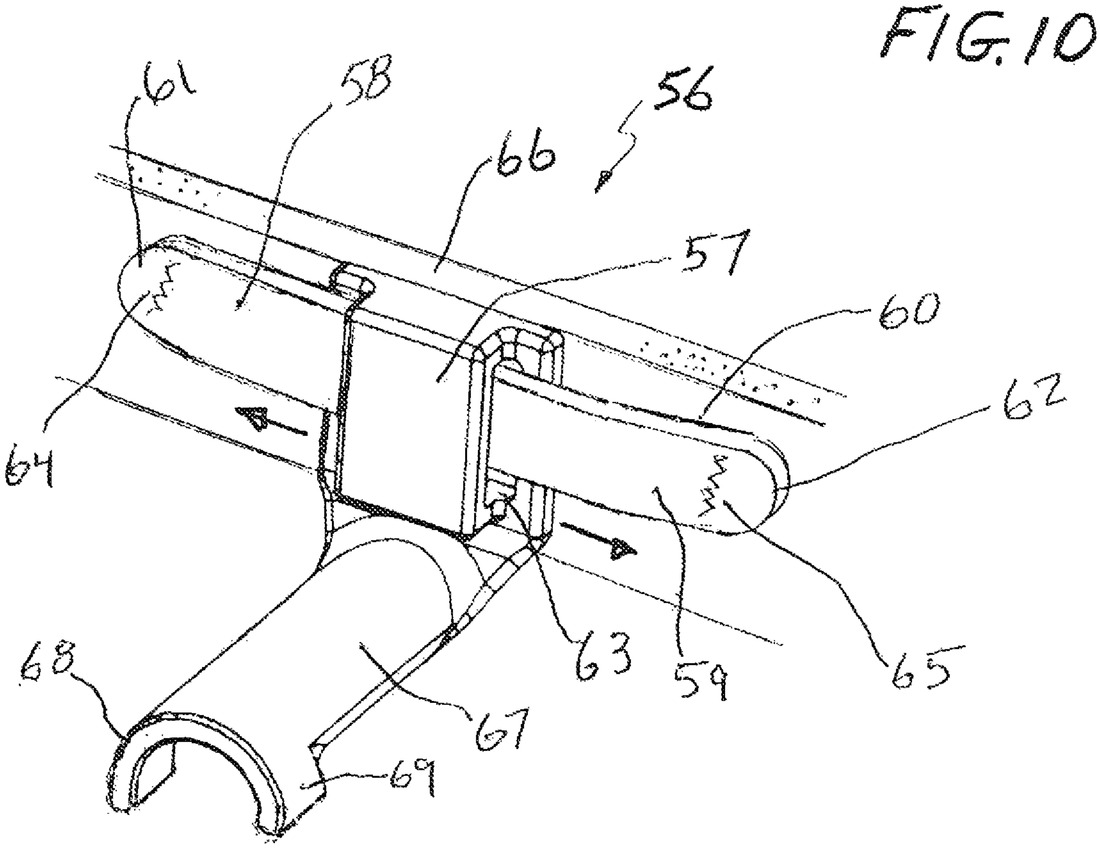
FIG. 10 is a partial perspective view of a commercial embodiment of the bracket assembly.

FIG. 10 depicts a commercial embodiment of the mechanism bracket assembly 56 having bracket portion 57 that incorporates a slide track member 58 utilizing a double sided knit loop. Both knit front side 59 and rear side 60 are laminated together to form a strong yet semi flexible slide track member 58 having both a soft loop front and rear side surface area permitting a smooth side to side slide action of slide track member 58 with a bracket portion 57. Slide track member 58 has die cut rounded ends 61 and 62 permitting ease of insertion during manufacturing assembly of slide track member 58 into and through bracket slot 63. Slide track member 58 is member tack stitched or sonic welded attached on both ends 64 and 65 onto cushioned neckband platform 66. Knit loop front side 59 on slide track member 58 will fully engage with the overlay strip 17 having rearward hook surface area 37 as previously shown, described, and depicted from FIGS. 4 and 5. Bracket portion 57 also incorporates bracket extension 67 which is about 1.750 inches long and terminates in shortened semi circular end tabs 68 and 69 which permit increased tube securement area to be tape in place. The bracket extension 67 is also referred to as a bracket extension channel or just a channel.

Figure 11:
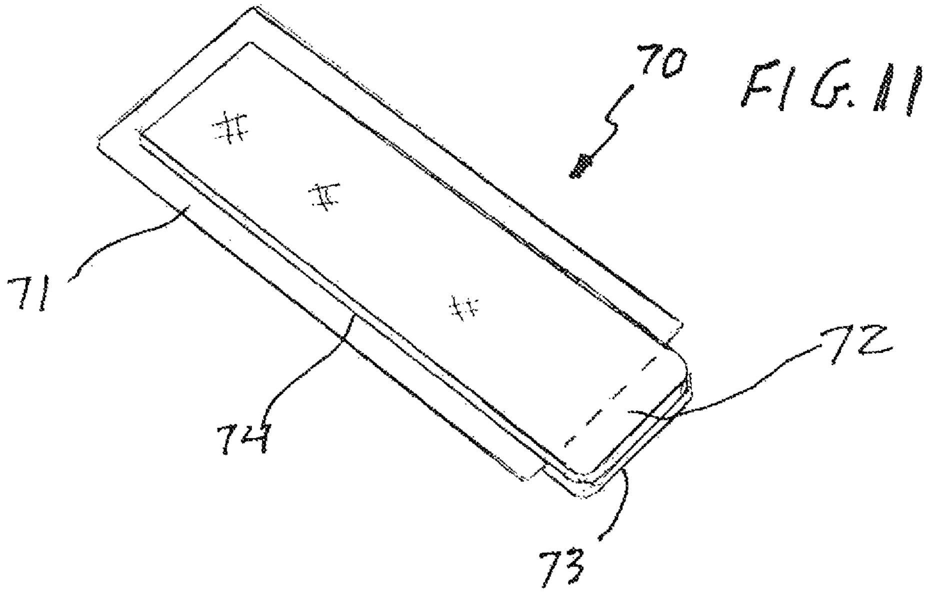
FIG. 11 is a perspective view of the commercially supplied bracket adhesive backed tape used for securement to the endotracheal tube.

FIG. 11 illustrates a singular specially fabricated endotracheal tube securement tape 70. Tape 70 may be an adhesive backed fabric tape made from fabric adhesive backed material, approximately 1 inch wide by 6 inches long and die cut on a factory release liner 71. Tape 70 terminates at its very end with a non-adherent tip 72 having a 3 mil mylar plastic underside backing 73. Tape 70 can be supplied in kit form along with adhesive backed anchoring device 21 as shown and described in FIGS. 1 and 3. Tape 70 uses an aggressive high tack synthetic rubber adhesive 74 which forms a strong adhesive bond with the PVC plastic material used both in the bracket extension channel 67 shown in FIG. 10 and most PVC endotracheal tubes 28 as shown and described from FIG. 1. Alternately, a mini roll of medical cloth tape can be substituted, supplied and packaged as an alternate tape securement means to tape 70.

Figure 12:
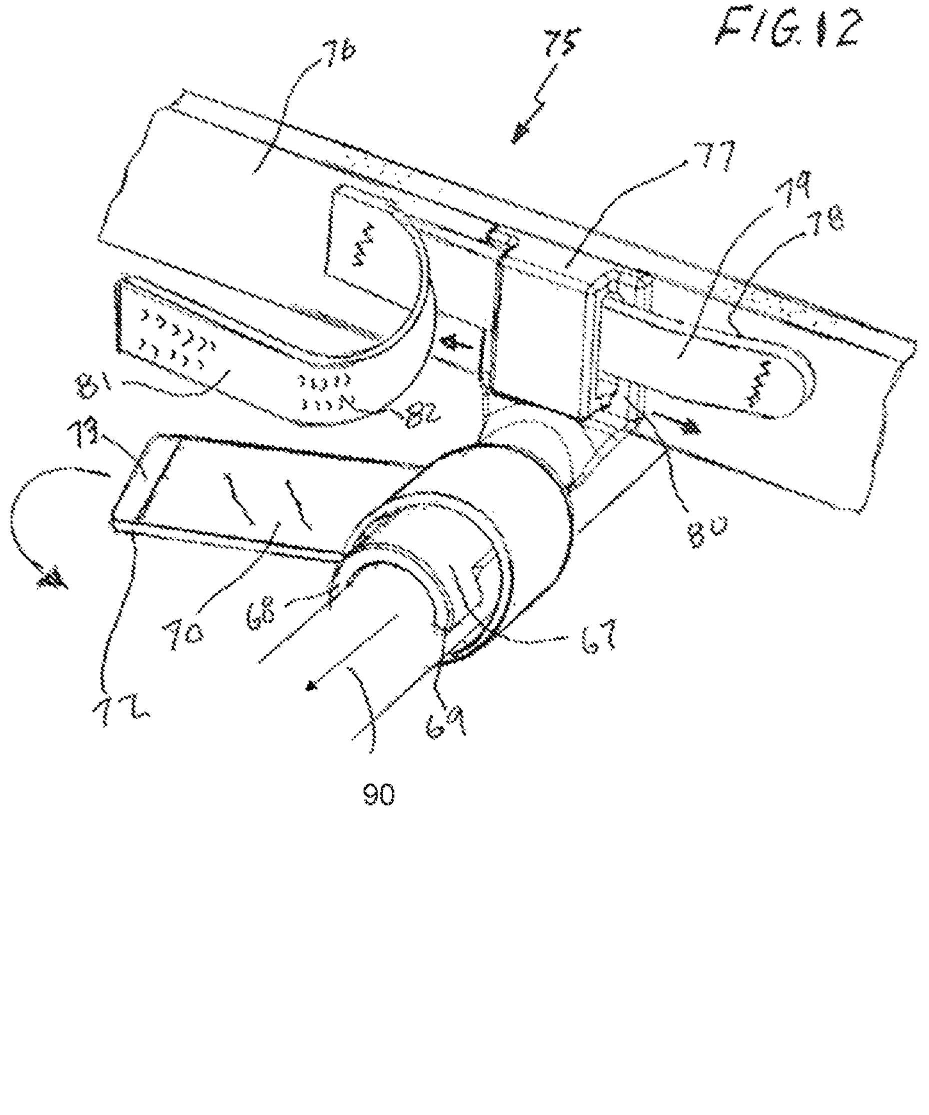
FIG. 12 is a partial perspective view of the bracket assembly from FIG. 10 depicting the tape from FIG. 11 utilizing the spiral taping method to secure the endotracheal tube to the bracket extension channel.

FIG. 12 illustrates the complete final commercial mechanism 75 incorporating the bracket assembly 56 from FIG. 10 and the adhesive backed tape 70 from FIG. 11. As can be seen from FIG. 12, there is illustrated a neckband platform portion 76 which is proximate to a patient's oral cavity wherein the mechanism assembly 77 is attached to the neckband portion 76. The mechanism assembly 77 incorporates a slide track member 78 having a frontal engagement surface 79. A bracket portion 80 is slideably moveable on the slide track member 78. A flexible overlay retention strip 81 has a rearward engagement surface 82 which matingly engages and disengages with the frontal surface 79 on slide track member 78. The rearward surface 82 on retention strip 81 overlays both the slide track member frontal surface 79 and the bracket portion 80.

As can be seen, the overlay retention strip 81 rearward surface 82 permits fixed positioning and slideable movement and repositioning of the bracket portion 80 when engaged or disengaged with the slide track member 78. Such slidable movement is in either direction, as illustrated by the arrow 35 and 36 of FIG. 3, normal to the axis 90 of the bracket extension 67 and endotracheal tube, as illustrated in FIG. 12. The mechanism assembly 77 permits fixed positioning when engaged and slideable repositioning when disengaged to another fixed position of the bracket portion 80. All of this takes place without the clinician having to remove the neckband platform portion 76 from the patient's face.

From FIG. 12, endotracheal tube 83 is secured in place within a patient's oral cavity utilizing bracket extension channel 67 and adhesive backed supplied tape 70. The instructions for the spiral motion application of the tape 70 to the bracket extension channel 67 and endotracheal tube 83 is clearly listed as part of FIG. 12.

Non-adherent tape tip 72 permits an easy finger grip tip to aid in application of the tape while 3 mil polyester plastic underside backing 73 on tape 70 offers a convenient lift off edge to permit removal of the tape from the bracket extension channel and tube when removal or replacement of the entire commercial mechanism 75 is required. Typically, this takes place once every three days or so.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Moreover, while illustrative embodiments have been described herein, the scope of any and all embodiments include equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. An endotracheal tube securement apparatus comprising:

a platform securable proximate a patient's oral cavity and having a forward facing surface, a slide track member having both a frontal facing surface and a rearward facing surface securable to the platform forward facing surface, a bracket retained between the platform forward facing surface and the slide track member rearward facing surface, and a retention strip having at least one end removably securable to both of the platform forward facing surface and the slide track frontal facing surface, said retention strip configured to retain said bracket in a fixed position when said retention strip overlays both the slide track member and the platform;

wherein said bracket is slideably moveable over the slide track member when one of the at least one ends of said retention strip is lifted off said slide track member and said platform.

2. The apparatus of claim 1 wherein the bracket defines a loop into which the slide track member is insertable.

3. The apparatus of claim 2 wherein the bracket has a generally L-shaped profile and the loop is formed therein with a pair of slots on a surface of the bracket.

4. The apparatus of claim 1 further comprising an anchor having a rearward facing surface configured for securing the platform above the patient's lips.

5. The apparatus of claim 1 wherein the platform is formed as a portion of a neckband securable about a head or neck of the patient.

6. The apparatus of claim 1 wherein first and second ends of the slide track member remain attached to the platform when the bracket is slideably moveable over the slide track member.

7. The apparatus of claim 1 wherein the slide track member frontal facing surface comprises at least one element configured for mating engagement and disengagement with at least one corresponding element of a rearward surface of the retention strip.

8. The apparatus of claim 7 wherein the slide track member forward facing surface comprises a loop pile material and the rearward surface of the retention strip comprises a hook material.

9. The apparatus of claim 1, wherein the platform is configured to be cushioned against the patient's oral cavity.

10. An endotracheal tube securement apparatus comprising:

a platform securable proximate a patient's oral cavity and having a forward facing surface, a bracket having a generally L-shaped profile with a first leg extending along an axis and securable to the endotracheal tube, the bracket further having a second leg retained relative to the platform forward facing surface but slidably movable in directions normal to the axis; and a retention strip having at least one end removably securable to both of the platform forward facing surface and a frontal facing surface of a slide track member, said retention strip configured to retain said bracket in a fixed position when said retention strip overlays both said slide track member and said platform;

wherein said bracket is slidably moveable over the slide track member when one of the at least one ends of said retention strip is lifted off the slide track member and the platform.

11. The apparatus of claim 10 wherein said slide track member has a rearward facing surface securable to the platform forward facing surface.

12. The apparatus of claim 10 wherein the second leg of the bracket defines a loop into which the slide track member is inserted.

13. The apparatus of claim 12 wherein the loop is formed therein with a pair of slots on a surface of the second leg of the bracket.

14. The apparatus of claim 10, wherein the platform is configured to be cushioned against the patient's oral cavity.

15. A kit for use in securing an endotracheal tube to a patient comprising:

an anchor having a rearward facing surface securable to a patient's skin;

a neck band having a rearward facing surface removably securable to the anchor and a forward facing surface to which a bracket is movably attached over a slide track member, the slide track member having first and second ends secured to the neck band forward facing surface, and a retention strip having at least one end removably securable to both of the neckband forward facing surface and a forward facing surface of the slide track member;

wherein said bracket is moveable over the slide track member when one of the at least one ends of the retention strip is lifted off said slide track member and said neck band, and wherein said retention strip configured to retain said bracket in a fixed position when said retention strip overlays both the slide track member and the platform.

16. The kit of claim 15 wherein the slide track member forward facing surface comprises at least one element configured for mating engagement and disengagement with at least one corresponding element of a rearward surface of the retention strip.

17. The kit of claim 16 wherein the slide track member forward facing surface comprises a loop pile material and the rearward surface of the retention strip comprises a hook material.

18. The kit of claim 15 wherein the anchor forward facing surface comprises at least one element configured for mating engagement and disengagement with at least one corresponding element of the neckband rearward facing surface.

19. The kit of claim 18 wherein the anchor forward facing surface comprises a hook material and the neckband rearward facing surface comprises a loop pile material.

20. The kit of claim 15, wherein at least a portion of the neck band is configured to be cushioned against an oral cavity of the patient.

* * * * *